(12) United States Patent
Ueyama et al.

(10) Patent No.: US 7,562,661 B2
(45) Date of Patent: Jul. 21, 2009

(54) HAIR WARMING TOOL AND HAIR TREATING METHOD

(75) Inventors: Kenichi Ueyama, Tokyo (JP); Akira Shiga, Tokyo (JP); Michiko Tada, Tokyo (JP)

(73) Assignee: Kao Corporation, Tokyo (JP)

( * ) Notice: Subject to any disclaimer, the term of this patent is extended or adjusted under 35 U.S.C. 154(b) by 81 days.

(21) Appl. No.: 10/082,343

(22) Filed: Feb. 26, 2002

(65) Prior Publication Data

US 2002/0157682 A1    Oct. 31, 2002

(30) Foreign Application Priority Data

Feb. 28, 2001 (JP) .............................. 2001-055990

(51) Int. Cl.
A45D 7/06 (2006.01)
A45D 2/36 (2006.01)

(52) U.S. Cl. .............................. 132/206; 132/220; 2/174

(58) Field of Classification Search ...................... 2/171, 2/174, 172, 200.1, 200.2, 204, 209.13, 209.14, 2/209.11, 175.4; 607/96, 98, 104, 109, 110, 607/112, 114; 132/221, 222, 206; 606/207, 606/220

See application file for complete search history.

(56) References Cited

U.S. PATENT DOCUMENTS

| | | | |
|---|---|---|---|
| 2,051,667 A | | 8/1936 | Worth |
| 2,153,671 A | | 4/1939 | Markel et al. |
| 2,431,882 A | * | 12/1947 | Morten ........................ 219/527 |
| 2,470,833 A | * | 5/1949 | Moore .......................... 34/95.1 |
| 2,493,363 A | * | 1/1950 | Sapp ........................... 34/95.1 |
| 2,497,301 A | * | 2/1950 | Farmer ......................... 34/95.1 |
| 2,783,806 A | * | 3/1957 | Andreadis .................... 607/110 |
| 3,682,181 A | * | 8/1972 | Garrett ........................ 132/220 |
| 4,093,424 A | * | 6/1978 | Yoshida et al. ................. 44/250 |
| 4,366,804 A | * | 1/1983 | Abe ......................... 126/263.02 |
| 4,382,446 A | * | 5/1983 | Truelock et al. ............. 607/110 |
| 4,459,471 A | * | 7/1984 | Hulett et al. ................. 219/527 |
| 4,580,547 A | * | 4/1986 | Kapralis et al. .......... 126/263.03 |
| 4,671,267 A | * | 6/1987 | Stout .............................. 602/2 |

(Continued)

FOREIGN PATENT DOCUMENTS

FR           898 294           4/1945

(Continued)

OTHER PUBLICATIONS

Patent Abstracts of Japan, JP 2000-189230, Jul. 11, 2000.

(Continued)

*Primary Examiner*—Eduardo C Robert
*Assistant Examiner*—David Comstock
(74) *Attorney, Agent, or Firm*—Oblon, Spivak, McClelland, Maier & Neustadt, P.C.

(57) ABSTRACT

A hair warming tool is in the form of sheet and has at least one heating part in the center thereof and a margin around said heating part. It is designed to wrap tied hair in said heating part and to be held in place to keep the wrapping state by fastening the margin with a fastening means such as an elastic band, a string or a wire. A hair treating method comprises wrapping tied hair with a hair warming tool of sheet form having at least one heating part while leaving at least the part of the hair near the roots unwrapped to warm the hair.

27 Claims, 2 Drawing Sheets

U.S. PATENT DOCUMENTS

| | | | | |
|---|---|---|---|---|
| 4,955,360 | A * | 9/1990 | Ogawa et al. | 126/263.02 |
| 5,129,391 | A * | 7/1992 | Brodsky et al. | 607/110 |
| 5,270,035 | A * | 12/1993 | Chimento | 424/70.8 |
| 5,480,418 | A * | 1/1996 | Zeoli-Jones | 607/110 |
| 5,741,318 | A * | 4/1998 | Ouellette et al. | 607/108 |
| 5,829,157 | A | 11/1998 | Gittens et al. | |
| 5,837,005 | A * | 11/1998 | Viltro et al. | 607/112 |
| 5,850,636 | A * | 12/1998 | Reuven | 2/174 |
| 6,099,556 | A * | 8/2000 | Usui | 607/114 |
| 6,132,454 | A | 10/2000 | Fellows | 607/96 |
| 6,182,294 | B1 * | 2/2001 | Pulley | 2/171 |
| 6,241,978 | B1 * | 6/2001 | Schlaeger | 424/70.2 |
| 6,287,545 | B1 * | 9/2001 | Su | 424/70.12 |
| 6,287,580 | B1 * | 9/2001 | Gott et al. | 424/401 |
| 6,500,201 | B1 * | 12/2002 | Tsuchiya et al. | 607/110 |
| 6,629,964 | B1 * | 10/2003 | Ono et al. | 604/304 |
| 2003/0041854 | A1 * | 3/2003 | Sabin et al. | 126/263.01 |

FOREIGN PATENT DOCUMENTS

| | | |
|---|---|---|
| GB | 538 948 | 8/1941 |
| JP | 07-048223 A | 2/1995 |
| JP | 8-24033 | 1/1996 |
| JP | 10-108719 | 4/1998 |
| JP | 2000-189230 A | 7/2000 |
| WO | WO 99/51174 * | 10/1999 |

OTHER PUBLICATIONS

Patent Abstracts of Japan, JP 2000-175728, Jun. 27, 2000.

* cited by examiner

HAIR WARMING TOOL AND HAIR TREATING METHOD

BACKGROUND OF THE INVENTION

This invention relates to a hair warming tool which allows a hair treatment preparation of the type that the effect is enhanced at a raised temperature to manifest its effect securely and selectively on a desired part of hair without causing discomfort or a burn due to heat and which is convenient for use at home, and to a hair treating method using the same.

Various types of hair warming tools for hair treatment have been proposed. For example, hair warming tools used for waving or curling hair include those capable of warming hair over the whole length from the roots to ends of hair and those capable of warming a partial length of hair. Partial hair warming for hair treatment is practiced by beauticians, etc.

Women of today, especially young women, tend to have their hair dyed, bleached or permed so frequently that their hair are apt to suffer from damage. Everyday use of a hair drier for drying or styling and excessive brushing also cause hair damage. In particular, tips of hair suffer from considerable damage, undergoing appreciable deterioration of physical properties such as strength and water retention, compared with other part of hair. It is therefore desirable that treatment for damaged hair be concentrated on hair tips rather than other part of hair.

JP-A-10-108719 discloses a method of warming a selected section of hair and a tool therefor. The hair warming tool disclosed is a hair warming cap partitioned into a plurality of sections. A user wears the cap with a disposable body warmer attached to sections where hair is to be warmed. However, the method of using the hair warming cap involves a fear of giving discomfort to a user or even causing a burn of the scalp by the generated heat. Further, the heating temperature cannot be set high. Furthermore, the hair warming cap is incapable of selectively heating a desired part of hair shafts, for example the tip of hair.

JP-A-8-24033 discloses a warming sheet which is composed of a base sheet having provided thereon a heat generating part and a sealing part both having a shape of a wide strip, the base sheet being folded along folding lines so that the sealing part is brought into contact with the heat generating part to seal the heat generating part. On use, the warming sheet is unfolded to strip the sealing part from the heat generating part and rolled up into a hot roll. A section of hair is rolled up on the hot roll to curl, or a section of hair is put on the heat generating part of the unfolded sheet and rolled up together with the sheet to curl. The warming sheet is not quick and easy to use for general consumers because a user has trouble making the warming sheet ready to use and also has difficulty in rolling her hair and fastening the roll by herself.

In short, conventional hair warming tools or hair treating methods are incapable of treating a selective portion of hair or inconvenient for general users to use at home from the standpoint of safety, manageability, cost, and the like.

SUMMARY OF THE INVENTION

An object of the present invention is to provide a hair warming tool and a hair treating method, with which a hair treatment preparation that enhances its effect under heat is made to exert its effect securely and selectively on a desired part of hair on a desired section of the head, which prevent discomfort or a burn due to the heat during hair treatment, and which are convenient to use.

To achieve the above object the present invention provides a hair warming tool of sheet form which has a heating part in the center thereof and a margin around the heating part and is designed to wrap tied hair in the heating part and to be held in place to keep the wrapping state by fastening the margin by means of a fastening means such as an elastic band, a string or a wire (hereinafter referred to as a first aspect of the present invention).

To achieve the above object, the present invention also provides a method of treating hair which comprises wrapping a tied section of hair with a hair warming tool of sheet form having at least one heating part while leaving at least the part of the hair near the roots unwrapped to warm the hair (hereinafter referred to as a second aspect of the present invention).

BRIEF DESCRIPTION OF THE DRAWINGS

The present invention will be more particularly described with reference to the accompanying drawings, in which.

DETAILED DESCRIPTION OF THE PREFERRED EMBODIMENTS

The hair warming tool according to the first aspect of the present invention has a sheet form and possesses at least one heating part. The shape of the sheet is not particularly limited. Conceivable shapes include angular shapes (a rectangle, a square and a polygon) which may have corners rounded or edges zigzagged, a circle, and an ellipse. A rectangular or square sheet is preferred for conformability to various sizes of buns or knots, ease of use, and advantageous for production.

While the size of the hair warming tool can be decided according to the length and volume of hair to be treated, a size of about 100 to 1200 $cm^2$ (in its plan view) is preferred considering applicability to various lengths and volumes of hair. Convenience of use taken into consideration, a size of 400 to 900 $cm^2$ is still preferred. For example, a rectangular (or square) hair warming tool having a side length of 20 to 30 cm is suitable.

The heating part is a part having a heat transfer material disposed therein. The heating performance of the heating part is not particularly restricted as long as the hair, either wet or dry, can be heated to 40° C. or higher. Seeing that the treatment is desirably completed in a short time for user's convenience, it is preferred that the temperature of wet or dry hair reach 40° C. or higher within 10 minutes, particularly within 5 minutes, from application of a hair treatment preparation.

The heat transfer material which is disposed in the heating part includes (1) heat generating materials which generate heat on chemical reaction, (2) heat generating materials which generate heat on phase change, for example, a structural change between crystal phase and an amorphous phase, such as sodium acetate trihydrate, (3) electrical heating elements which generate heat on electricity application, (4) heat storage materials, such as polyethylene glycol, (5) water-containing materials which, when heated, are capable of retaining heat, such as silica gel, and (6) materials utilizing far-infrared radiation heat. Preferred of them are the heat generating materials (1). From the standpoint of convenience to use (ease of making the tool ready to use simply by opening the seal) and safety, those capable of generating heat on contact with air is (oxygen and water vapor) are particularly preferred. A suitable heat generating material which generates heat on contact with air is a heat generating composition containing iron powder that has been used in disposable body warmers (hereinafter sometimes referred to as a powdered heating element). A typical formulation of the powdered heating element is: 10 to 80 wt % iron powder, 1 to 30 wt % activated carbon (or non-activated carbon or a mixture of them), 0.1 to 15 wt % metal salts (e.g., sodium chloride), and 1 to 50 wt % water. The composition can further contain inorganic powder (e.g., vermiculite), a water retentive material (e.g., a water-absorbing polymer), etc. In what follows, all the percents are by weight unless otherwise noted.

The powdered heating element which is preferred for heating hair to 40° C. or higher within 10 minutes comprises 40 to 60% iron powder, 1.0 to 3.0% sodium chloride, 1.0 to 5.0% activated carbon, 3.0 to 5.0% a water-absorbent polymer, and 3.0 to 10.0% vermiculite. It is desirable that the heating element cool down rapidly after use, particularly to a temperature below 40° C. within 1 hour after use. In order for the powdered heating element to heat up to 40° C. or above within 10 minutes and to cool below 40° C. within 1 hour, the powdered heating element is preferably used in an amount of 0.05 to 0.3 g per $cm^2$ of the heating part. It is preferred for the powdered heating element to be packed uniformly.

On the other hand, the above-described heat transfer materials (2) to (6) are advantageous in that they are repeatedly usable.

In using the powdered heating element mainly comprising iron powder, the hair warming tool should be packaged in a bag made of a film having high gas barrier properties because the heating part will be deteriorated on contact with water vapor or air before use. It is preferred for the bag to have a water vapor barrier property of 50 $g/m^2 \cdot day$ or less in terms of water vapor transmission rate as measured according to JIS Z0208 (B method; 40° C., 90% RH) and an oxygen barrier property of 20 $cc/m^2 \cdot day$ or less in terms of gas transmission rate as measured according to JIS K7126 (23° C., 90% RH). Suitable materials for making the packaging bag include, but are not limited to, a synthetic resin/inorganic barrier layer composite and an aluminum laminate film.

The heating part or parts preferably have a total area of 40 $cm^2$ or more, particularly 100 $cm^2$ or more, for effective hair warming. The upper limit of the total heating area is preferably, while not limited to, 800 $cm^2$, particularly 600 $cm^2$.

While the hair warming tool can have one or more than one heating parts, it is preferred for the hair warming tool to have a plurality of heating parts to have improved flexibility for wrapping tied hair. By having a plurality of heating parts, the hair warming tool becomes flexible and conformable to the contour of the section of hair to be treated, and can be folded into a compact package. Where the hair warming tool has two or more heating parts, each heating part preferably has an area of 5 to 200 $cm^2$, particularly 10 to 100 $cm^2$, for securing both flexibility of the tool and a sufficient total heating area. The width W1 or open space (see FIG. 1) between adjacent heating parts is preferably 1 to 40 mm, still preferably 3 to 20 mm, so as to provide flexibility and to secure a sufficient area for the margin used to fasten the hair warming tool (the area of prescribed width having no heating part).

The heating part may have any arbitrary shape, such as a circle, a rectangle, a diamond or a polygon. Two or more heating parts may be arranged close to each other or scattered in groups.

The total area ratio of the heating part(s) in the hair warming tool (in a plan view) is preferably 5 to 70%, particularly 10 to 40%, so as to secure a sufficient heating area and a sufficient margin as a fastening area in good balance.

The expression "to wrap tied hair (or a tied section of hair) in a heating part" is intended to include the way of wrapping tied hair or a tied section of hair in a plurality of heating parts.

Figure 1:
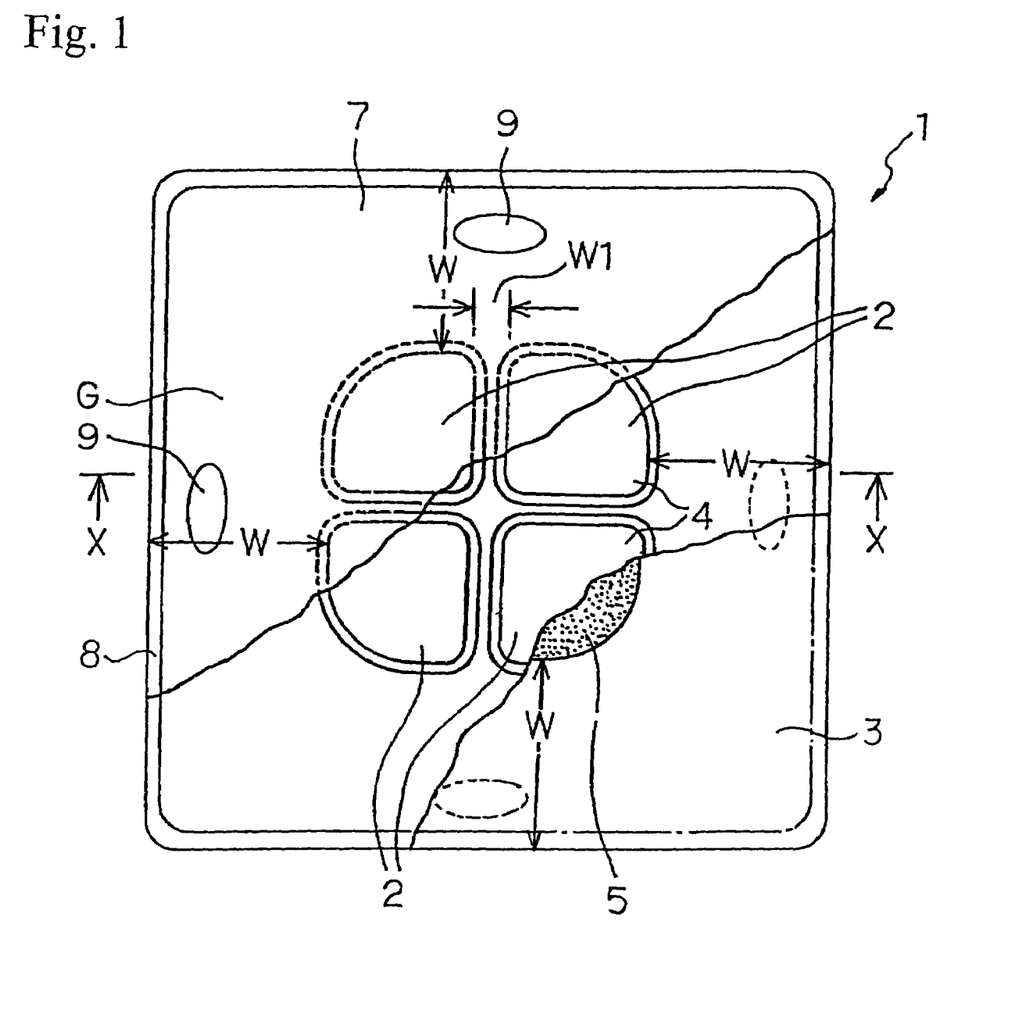
FIG. 1 is a plan view showing an embodiment of the hair warming tool according to the present invention, with a part cut-away.

The hair warming tool preferably comprises a base sheet 3 which provides the surface side or the reverse side of the hair warming tool and at least one heat transfer material 5, which forms at least one heating part 2, fixed on a prescribed site of the base sheet 3 as shown in FIG. 1.

The heat transfer material can be fixed on the base sheet 3 by direct adhesion, or by interposing between the base sheet and another sheet, or by inserting into a pocket made on the base sheet. Where the heat transfer material is adhered to the base sheet or inserted into a pocket, it may be disposed on either side of the base sheet (the surface side that faces outward while worn or the reverse side that is brought into contact with hair).

In using the above-described powdered heating element as a heat transfer material, the powder put into a flat bag made of an oxygen-permeable sheet or a commercially available body warmer can be adhered directly to the base sheet or put into a pocket made on the base sheet. For bringing the hair warming tool into good contact with hair to achieve effective heating, it is preferred that a powdered heating element be interposed between a plurality of sheets. In this embodiment, the sheet(s) on at least one side of the powdered heating element should be gas-permeable to allow oxygen necessary for heat generating reaction to pass through. The gas-permeable sheet which is disposed outside (the sheet in direct contact with open air and the sheet in direct contact with hair) preferably has water resistance or water repellency.

The material of the base sheet is not particularly limited as long as the sheet is flexible and capable of wrapping a knot or a bun of hair. Considering that the sheet comes into contact with hair wetted with water or a hair treatment preparation, water-resistant or water-repellent materials are preferred. Suitable materials include synthetic resins (e.g., linear low-density polyethylene (LLDPE), low-density polyethylene, (LDPE) high-density polyethylene (HDPE), polyprene, polypropylene ionomers, polystyrene, ethylene-(meth) acrylic acid copolymers, polyester such as polyethylene terephthalate, polyvinyl chloride, and polyvinylidene chloride; copolymers comprising these resin components; and laminates or composites thereof), paper, metals (e.g., aluminum), and fabrics (e.g., nonwoven fabric). These materials can be used either individually or as a laminate thereof.

The gas-permeable sheet preferably has a gas permeability of about 1,000 to 20,000 $g/m^2 \cdot 24$ hr in terms of water vapor transmission rate as measured according to JIS Z0208 (B method; 40° C., 90% RH) or about 1 to 500 sec/100 ml in terms of air permeance as measured according to Japan TAPPI No. 5-74B method.

As shown in FIG. 1, the hair warming tool according to the first aspect of the invention has a margin G where no heating part is disposed (an area of prescribed width used for fastening) in the peripheral portion thereof, i.e., around the heating part(s). The term "width" as referred to here is the distance from an edge of the hair warming tool to the nearest heating part, being indicated by symbol W in FIG. 1. In order to facilitate fastening the hair warming tool around a knot of hair and to prevent the heating part 2 from coming into contact with the skin, the width of the margin G is preferably at least 1 cm, still preferably 3 to 15 cm, particularly preferably 5 to 12 cm, over the whole periphery. The width W of the margin G does not need to be the same over the whole periphery of the hair warming tool.

Figures 3A, 3B, 3C, 3D, 3E:
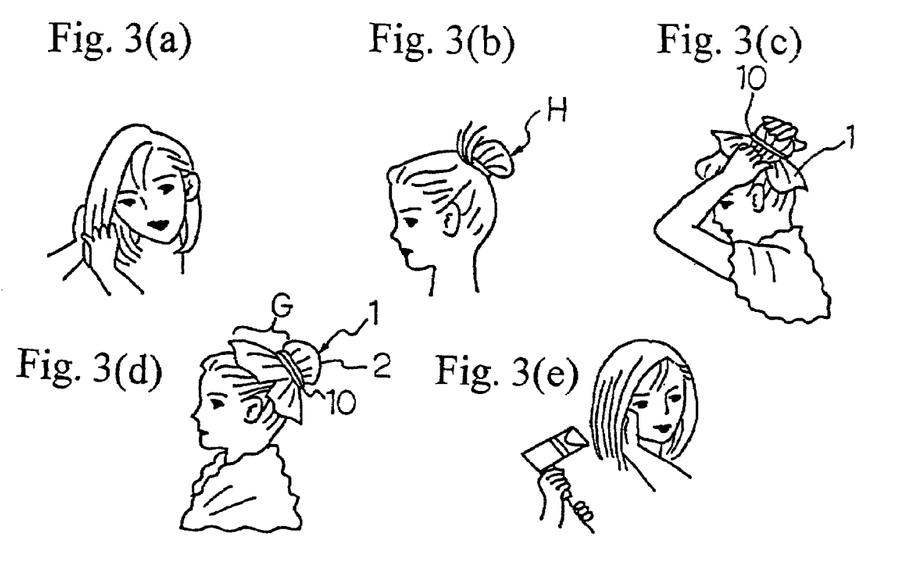
FIG. 3 illustrates the procedure for carrying out hair treatment according to an embodiment of the hair treating method of the present invention, which also presents an example of usage of the hair warming tool shown in FIG. 1.

As shown in FIGS. 3(*b*) to 3(*d*), the hair warming tool according to the present invention is used to wrap hair tied into a knot in its heating part. The wrapping state is kept by fastening the margin G around the knot with a fastening means, such as an elastic band, a string, a tape or a wire.

The manner of tying hair is not particularly restricted, and the whole hair or any desired amount of hair is tied into a knot. A suitable manner of tying hair will be described later with respect to the second aspect of the invention. A suitable manner of wrapping a bun or a knot of hair will also be described later.

The fastening means is used to fasten the margin around the knot to keep the hair warming tool in place. It may be an independent member separately prepared or a member previously attached to the hair warming tool. The elastic band as a fastening means includes commercially available "hair-friendly" elastic bands and generally used rubber bands. Any string or tape fit for fastening can be used. A water-resistant and heat-resistant string or tape is preferred. Any wire that is flexible and fit for securely tying the hair warming tool can be used. A drawstring is an example of the fastening means previously attached to the hair warming tool.

In the hair treating method according to the second aspect of the present invention, tied hair is wrapped with a warming tool of sheet form having at least one heating part while leaving at least the part of hair near the roots unwrapped to warm the hair. Usually, a hair treatment preparation is previously applied to the hair to be wrap-treated. A hair treatment preparation may be applied mainly to the tips of hair or over the whole length of hair. The hair to be treated with the hair treatment preparation may be either dry or damp, which depends on the properties of the preparation or the aimed effects.

The manner of tying hair is not restricted, and a desired amount of hair can be tied in a usual way, just like a woman with medium long hair gathering her hair into a knot or a bun and securing with an elastic band, hair pins, etc. For example, a desired amount of hair can be gathered up into a ponytail and held at one or more positions. Or the ponytail can be rolled up or down into a loop and held in place or coiled around the base of the ponytail into a bun and held in place.

A particularly preferred way of tying hair is shown in FIG. 3(*b*). The bundle of hair can be held with an elastic band, hairpins, a tape or yarn.

The knot or bun of hair is wrapped in a warming tool of sheet form having a beating part while leaving the hair near the roots unwrapped. The hair warming tool according to the first aspect of the invention is a preferred warming tool. The term "near the roots" is used to describe the part of hair from the scalp up to about 3 mm. The knot or bun is preferably wrapped so that the ends of hair of that section are completely put into the closed space formed by the fastened warming tool. Other part of hair than the ends, for example, the middle part of hair other than the roots and the ends may be wrapped selectively.

The warming tool wrapping the tied hair can be fixed by any means. For example, the warming tool can be fastened by the fastening means as described with reference to the first aspect of the invention, such as an elastic band, or hair pins.

The fastening means such as pins, a tape, a string or elastic band may previously be attached to the warming tool of sheet form.

The heating temperature can be selected according to the purpose of treatment or the kind and the properties of the hair treatment preparation applied. For example, a temperature around 45 to 60° C. is preferred. The heating time is also selected according to the purpose of the treatment or the kind and the properties of the hair treatment preparation. For example, a heating time of about 3 to 30 minutes is preferred.

After completion of the warming treatment, the hair can be finished in any desired manner. The hair treatment preparation may be rinsed off or left in.

The hair treatment preparation, which can be applied either before or after tying hair, includes various known hair care products, such as rinse-off conditioners or leave-in conditions for improving the feel of hair or for repairing damaged hair, hair colors (including bleaches and non-permanent colors), permanent waving solutions, and styling products (e.g., gels, creams, sprays and mousses). The hair treating method of the present invention is effective particularly for treating hair with preparations containing at least one oiliness compound, especially treatment conditioners for improving the feel of hair or for treating damaged hair.

Oiliness compounds that have commonly been used in various hair care products which are insoluble in water can be used in the present invention. The following is a list of preferred oiliness compounds.

1) Higher alcohols having a straight-chain alkyl group containing 14 to 22, preferably 16 to 22, carbon atoms, such as cetyl alcohol (cetanol), stearyl alcohol, cetostearyl alcohol, behenyl alcohol, and other aliphatic alcohols. A preferred content of the higher alcohol in the preparation is 0.5 to 10%.

2) Ester oils, such as isopropyl palmitate, isopropyl myristate, octyldodecyl myristate, cetyl stearate, cholesteryl lanoline fatty acid esters, cetyl oleate, dipentaerythritol fatty acid esters, and myristyl lactate. A preferred content of the ester oil in the preparation is 0.5 to 10%.

3) Hydrocarbon oils, such as liquid paraffin, isoparaffin, light isoparaffin, squalane, and squalene. A preferred content of the hydrocarbon oil in the preparation is 0.1 to 10%.

4) Natural or synthetic waxes, such as hardened castor oil, beeswax, carnauba wax, lanoline, reduced lanoline, candelilla wax, sugar cane wax, Shellac wax, cholesteryl isostearate, cholesterol, and modified cholesterol. A preferred content of the wax in the preparation is 0.1 to 10%.

5) Other oiliness compounds, such as natural fats and oils mainly made of triglycerides, e.g., avocado oil, tsubaki oil, turtle oil, macademian nuts oil, olive oil, egg yolk oil, safflower oil, jojoba oil, sesame oil, rapeseed oil, linseed oil, cocoa butter, and palm oil. A preferred content of the fat and oil in the preparation is 0.1 to 10%.

These oiliness compounds can be used either individually or as a combination of two or more thereof. It is particularly preferred for the hair treatment preparation to contain a wax at the above-specified content. A preferred total content of the oiliness compounds in the hair treatment preparation is 0.5 to 30%, particularly 3.0 to 20.0%, especially 3.0 to 15%.

It is preferred for the hair treatment preparation to contain an acid, especially an organic acid. Acids that can be incorporated into the preparations include organic acids, such as glycolic acid, lactic acid, citric acid, malic acid, tartaric acid, and acetic acid; and inorganic acids, such as phosphoric acid and hydrochloric acid. These acids can be used either individually or as a combination thereof. Of the acids, malic acid is especially effective in healing inside damage of hair to improve the sheen or feel. A preferred content of the acid in the preparation is 0.01 to 2%, particularly 0.01 to 1%.

A low pH preparation brings increases hair improving effects. A preferred pH is from 2 to 4.5, particularly 2.5 to 4.0. A pH lower than 2 has a possibility of skin irritation.

It is preferred for the hair treatment preparation to contain an organic solvent. Preferred organic solvents include lower alcohols having a hydroxyl group which are liquid at ambient temperature and have 2 to 6 carbon atom, aromatic alcohols, alkylene carbonates, such as propylene carbonate, and N-methylpyrrolidone. Particularly preferred are aromatic alcohols, such as benzyl alcohol, 2-benzyloxyethanol, phenoxyethanol, 2-phenylethyl alcohol, phenylpropanol, cinnamic alcohol, α-methylbenzyl alcohol, and dimethylbenzylcarbinol. These solvents can be used either individually or as a combination thereof The organic solvent helps the components of the hair treatment preparation penetrate into hair. A recommended content of the solvent in the hair treatment preparation is 0.1 to 20%, particularly 0.5 to 10%.

Preferred hair treatment preparations comprise at least one of the above-described oiliness compounds, at least one of the above-described acids in the respective preferred amounts and, in addition, 0.1 to 5% of a cationic surface active agent, and 0.1 to 5% of silicone.

Any cationic surface active agents that dissolve in water to provide a cationic atomic group, such as alkylamine salts and quaternary ammonium salts, can be used. Examples of useful cationic surface active agents are stearic diethylaminoethylamide lactate, stearic dimethylaminopropylamide citrate, stearyltrimethylammonium chloride, distearyldimethylammonium chloride, cetyltrimethylammonium chloride, cetyldimethylbenzylammonium chloride, behenyltrimethylammonium chloride, stearyltrimethylammonium bromide, and lanoline fatty acid aminopropylethylammonium ethylsulfate.

The silicone includes dimethyl polysiloxane, methylhydrogen polysiloxane, methylphenyl polysiloxane, polyether-modified organopolysiloxanes, fluoroalkyl·polyoxyalkylene-comodified organopolysiloxanes, alkyl-modified organopolysiloxanes, dimethiconol, terminal-modified organopolysiloxanes, fluorine-modified organopolysiloxanes, amodimethicone, amino-modified organopolysiloxanes, silicone gel, acrylic silicone, trimethlsiloxysilicic acid, silicone RTV rubber, and fluorine-modified silicone resins.

When the hair treatment preparation is an emulsion formulation, it is preferred that the preparation have a demulsifying temperature of 55 to 60° C. so that the emulsified state may be broken when heated to the demulsifying temperature to exhibit enhanced adsorption to or penetration into hair, thereby bringing about marked enhancement of the treatment. The demulsifying temperature is the temperature of an endothermic peak (main peak) of a DSC differential scanning calorimetry curve measured at a temperature rise rate of 3° C./mm.

The hair treatment preparation can further contain other ingredients. The other ingredients include those commonly employed in ordinary hair treatment preparations, such as polymers, thickeners, anionic, nonionic or amphoteric surface active agents, polyhydric alcohols, powders (e.g., pigments, colorants and resins), fluorine compounds, antiseptics, perfumes, humectants, physiologically active components, salts, antioxidants, chelating agents, neutralizers, and pH adjustors.

Useful polyhydric alcohols include ethylene glycol, polyethylene glycol, propylene glycol, dipropylene glycol, polypropylene glycol, glycerol, diglycerol, 3-methyl-1,3-butanediol, 1,3-butylene glycol, sorbitol, glucose, sucrose, fructose, xylitol, lactose, maltose, trehalose, sulfated trehalose, and chemically modified products of these alcohols. A suitable polyhydric alcohol content in the hair treatment preparation is about 1 to 10%.

The present invention will now be illustrated in greater detail with reference to Examples.

EXAMPLE 1

Figure 2:
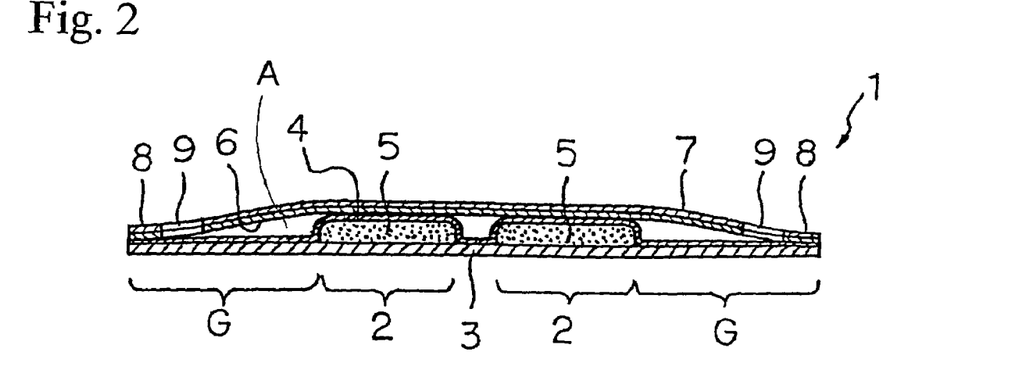
FIG. 2 is a cross-sectional view taken along line X-X in FIG. 1.

Preparation of Hair Warming Tool:

A hair warming tool 1 having the structure shown in FIGS. 1 and 2 was prepared. The hair warming tool 1 shown in FIGS. 1 and 2 is made up of a base sheet 3 having a rectangular shape with rounded corners, powdered heating elements 5 (as a heat transfer material) which are fixed on one side of the base sheet 3, being sealed between the base sheet 3 and another sheet 4, and two sheets covering the heating elements 5 (a first sheet 6 and a second sheet 7). The hair warming tool 1 has four heating parts 2 in the central portion thereof, each formed of the fixed powdered heating element 5.

Since the powdered heating element used as a heat transfer material needs air for heat generation, the sheet 4 is permeable to gas. The base sheet 3 is moisture resistant and water repellent for applicability to wet hair. The sheet 4 has moisture resistance and water repellency for use in a bathroom or a like atmosphere.

The first sheet 6 and the second sheet 7 are provided for safety (for preventing, e.g., powder leaks), convenience to use, and decoration. Should the peripheral seal of the heating part 2 be broken, the first sheet 6 serves to prevent the powder from leaking. The first sheet 6 can be printed with logotypes, etc. to add a decorative design. The second sheet 7 is made of a material having low thermal conductivity, such as nonwoven fabric. Where the heating element is designed to have a temperature increased to about 60° C., it may be felt slightly too hot to the touch while worn, in which case the second sheet 7 will serve as an insulator. For this heat insulation function, nonwoven fabric is suitable as the second sheet 7. If the sheet 6 has low air permeability, there is a possibility of the sheet 6 expanding due to steam generated from the heating elements and expansion of air around the heating elements because the periphery of the sheet 6 is sealed (indicated by numeral 8). It is therefore preferred for that kind of sheet 6 to have holes 9, which open into air gap A, for air escape. The first sheet 6 and/or the second sheet 7 may be omitted.

In this example, the margin G where no heating parts is disposed had a least width W (see FIG. 1) of 6 to 9 cm.

Materials for making the base sheet 3 include those having both water resistance and flexibility, such as polyethylene, polypropylene, and polyvinyl chloride. Materials for making the sheet 4 include known air-permeable sheets customarily used for general disposable body warmers, such as a nonwoven fabric sheet.

Hair Treating Method:

Hair softeners having the following formulations (preparations 1 and 2) were prepared.

1) Preparation 1

| | |
|---|---|
| Cetyltrimethylammonium chloride (30% aqueous solution) | 1.5% |
| Sorbitan monostearate | 2.0% |
| Cetanol (oiliness compound) | 1.5% |
| Concentrated glycerol | 5.0% |
| Dimethicone | 0.5% |
| Glycolic acid (71% aqueous solution) | 0.05% |
| Purified water | balance |
| pH | 3.8 |

2) Preparation 2

| | |
|---|---|
| Cetyltrimethylammonium chloride (30% aqueous solution) | 1.5% |
| Sorbitan monostearate | 2.0% |
| Cetanol (oiliness compound) | 1.5% |
| Concentrated glycerol | 5.0% |
| Isopropyl palmitate (oiliness compound) | 1.0% |
| Paraffin (oiliness compound) | 0.5% |
| Cholesteryl isostearate (oiliness compound) | 0.5% |
| Dimethicone | 0.5% |
| Glycolic acid (71% aqueous solution) | 0.05% |
| Malic acid (50% aqueous solution) | 0.05% |
| Purified water | balance |
| pH | 3.7 |

Evaluation of Improvement on Slipperiness and Smoothness in Finger Combing:

Three bundles of hair of about 30 cm in length and 10 g in weight were prepared for evaluation, each from Japanese women's hair having been permed or bleached and suffering from damage at the tips. Each bundle of hair was treated with a commercially available shampoo (Lavenus Silky Supply Shampoo, available from Kao Corp.) and then with a commercially available rinse conditioner (Lavenus Silky Supply Rinse, available from Kao Corp.) and towel-dried to remove excess water. One gram each of preparations 1 and 2 was applied to two of the bundles. The bundle with the preparation applied was tied with an elastic band into a knot. The hair warming tool 1 which had been packaged in a gas-barrier bag was taken out of the package, wrapped over the knot of hair, and secured with an elastic band to heat the hair for 15 minutes. The warming tool was removed, and the hair bundle was completely dried with warm air from a hair dryer and evaluated organoleptically. The materials used to make the hair warming tool were as follows.

| | |
|---|---|
| Base sheet 3: | A composite sheet of nonwoven fabric made of polyethylene terephthalate (PET)/polyethylene (PE) laminated with a sheet made of LDPE. |
| Heating element 5: | A powdered heat generating composition comprising 50.0% iron powder, 34.4% ion-exchanged water, 1.6% sodium chloride, 2.0% activated carbon, 7.0% vermiculite, and 5.0% a water-absorbing polymer. |
| Sheet 4: | A gas-permeable sheet made of HDPE and PP/PE (air permeance: 45 sec/100 ml). |
| Sheet 6: | A polyethylene sheet containing calcium carbonate (water vapor transmission rate: 2.2 g/100 cm$^2$/hr). |
| Sheet 7: | Spun-bonded nonwoven fabric made of PET/PE |

A panel of 10 experts evaluated the degree of improvement in smooth and easy finger combability of the hair bundles treated with preparations 1 and 2 over the untreated hair bundle and scored according to the following standard of evaluation. An average of the scores given by 10 members was obtained.

Standard of Evaluation:

5 . . . Fairly better
4 . . . Slightly better
3 . . . Neither better nor worse
2 . . . Slightly worse
1 . . . Fairly worse As a result, the hair bundles treated with preparations 1 and 2 scored 4.1 points and 4.7 points, respectively. As can be seen from these results, while treatment with preparation 1 achieves an improvement, the hair warming treatment with the hair warming tool is more effective in using preparation 2, which contains an ester oil or an oiliness compound that is semisolid or solid at room temperature.

EXAMPLE 2

(Treatment 1)

A panel of 10 experienced testers, all wearing their hair medium to long and suffering from dry and unmanageable hair, washed their hair using hair care products they usually use (i.e., a shampoo, a rinse conditioner, a treatment conditioner, etc.). After towel drying, they applied preparation 2 to their hair and the hair was styled as usual without rinsing off the treatment preparation.

(Treatment 2)

Figure 4A:
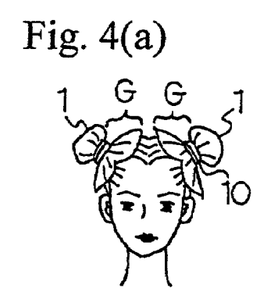
FIG. 4 illustrates another usage of the hair warming tool shown in FIG. 1.
Figure 4B:
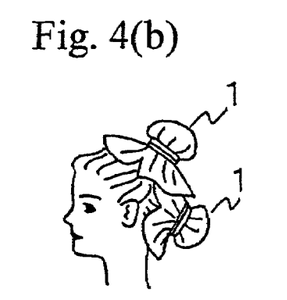

The testers washed their hair to completely get rid of preparation 2 and then followed instructions of a manual describing the procedure shown in FIGS. 3(a) to (e) by using preparation 2, two hair warming tools 1, and four elastic bands 10. In detail, preparation 2 was applied to hair as shown in FIG. 3(a), and the hair was gathered up and tied into a knot H as shown in FIG. 3(b). The hair warming tool was taken out of the package made of a gas-barrier material and wrapped over the knot while leaving the roots of hair unwrapped, and the margin G of the hair warming tool 1 was fastened with the elastic bands 10 as shown in FIG. 3(c). The knot of hair was heated in this state for about 15 minutes (heating temperature: 60° C.) as illustrated in FIG. 3(d). After the heating treatment, the hair was styled as usual without rinsing off the treatment preparation as shown in FIG. 3(e). The ten testers managed to carry out the series of procedures according to the manual with no difficulty. Two out of ten testers were instructed to divide their hair into two sections and treat each section as described above as illustrated in FIG. 4(a) using two hair warming tools 1, and the eight others were instructed to make a single knot and to use a single hair warming tool 1. FIG. 4(b) depicts another way of making two knots of hair.

Evaluation of Treated Hair:

The testers rated their hair after the treatment 1 in terms of moisturized feel in comparison with the hair condition before the treatment 1 according to the following standard. Similarly, the testers rated their hair after the treatment 2 in terms of moisturized feel in comparison with the hair condition before the treatment 1 according to the following standard. An average of the scores given by 10 testers was obtained.

Standard of Evaluation on Moisturized Feel:

5 . . . Fairly better
4 . . . Slightly better
3 . . . Neither better nor worse
2 . . . Slightly worse
1 . . . Fairly worse Evaluation of Manageability:

The testers rated their hair after the treatment 1 or the treatment 2 in terms of manageability according to the following standard. An average of the scores given by 10 testers were obtained.

Standard of Evaluation on Manageability:
5 . . . Fairly better
4 . . . Slightly better
3 . . . Neither better nor worse
2 . . . Slightly worse
1 . . . Worse As a result, treatment 2-treated hair (Example) scored 4.6 points in moisturized feel and 4.7 points in manageability, whereas treatment 1-treated hair (Comparative Example) scored 3.7 points in moisturized feel and 4.1 points in manageability. As is proved from these results, while hair treating effects are produced without hair warming, the effects of the hair treatment preparation are enhanced under heat. It is also seen that the feel of hair can be improved by warming a necessary part of hair without warming the whole hair. None of the testers complained of heat during the treatment 2.

EXAMPLE 3

A preshampoo conditioner having the following formulation (preparation 3) was prepared.

Preparation 3

| | |
|---|---|
| Malic acid (50% aqueous solution) | 8.0% |
| 2-Benzyloxyethanol | 10.0% |
| 95% Ethanol | 15.0% |
| Hydroxypropyl xanthan gum | 2.0% |
| Aqueous sodium hydroxide solution (48%) | for adjusting pH to 3.0 |
| Purified water | balance |
| pH | 3.0 |

Evaluation of Improvement in Slipperiness of Tips, Smoothness in Finger Combability and Sheen Two bundles of hair of about 30 cm in length and 25 g in weight were prepared for evaluation, each from a German woman's blonde hair having been bleached and suffering from damage. 25 grams of preparation 3 was applied to one of the bundles of hair and tied with an elastic band. The same hair warming tool as used above which had been sealed in a gas-barrier bag was taken out of the bag, wrapped over the tied bundle of hair, and secured with an elastic band to heat the hair for 15 minutes. The hair bundle was removed from the warming tool, rinsed with warm water to remove the preparation, shampooed with a commercially available shampoo (Lavenus Supply Shampoo, available from Kao Corp.), and treated with a commercially available rinsing conditioner (Lavenus Silky Supply Conditioner, available from Kao Corp.). After the treatment, towel-dried hair was completely dried with a hair dryer.

The treated hair bundle was evaluated in terms of improvement in slipperiness of tips, finger combability and sheen as compared with the other hair bundle that had been shampooed, treated with the rinse conditioner but not treated with preparation 3 and rated according to the following standard. An average of the scores given by 10 testers was obtained.

Standard of Evaluation:
5 . . . Fairly better
4 . . . Slightly better
3 . . . Neither better nor worse
2 . . . Slightly worse
1 . . . Fairly worse As a result, the preparation 3-treated hair scored 4.5 points (the score of the untreated hair was 3.0 points) in the evaluation of improvement in slipperiness of tips and finger combability. The preparation 3-treated hair scored 4.8 points (the score of the untreated hair was 3.0 points) in the evaluation of improvement in sheen.

EXAMPLE 4

A postshampoo conditioner having the following formulation (preparation 4) was prepared.

| Preparation 4 | |
|---|---|
| Cetyltrimethylammonium chloride (30% aqueous solution) | 1.5% |
| Sorbitan monostearate | 2.0% |
| Cetanol (oiliness compound) | 1.5% |
| Concentrated glycerol | 5.0% |
| Isopropyl palmitate (oiliness compound) | 1.0% |
| Paraffin (oiliness compound) | 0.5% |
| Cholesteryl isostearate (oiliness compound) | 0.5% |
| Dimethicone | 0.5% |
| 2-Benzyloxyethanol | 0.3% |
| Glycolic acid (71% aqueous solution) | 0.05% |
| Malic acid (50% aqueous solution) | 0.05% |
| Purified water | balance |
| pH | 3.7 |

Preparation 4 was evaluated in the same manner as for preparations 1 and 2.

The Results Obtained were as Follows.
Slipperiness and finger combability 4.9

| | |
|---|---|
| Moisturized feel | 4.8 |
| Manageability | 4.9 |

The treated hair bundle was evaluated in terms of improvement in slipperiness of tips and finger combability in the same manner as in EXAMPLE 1 except that preparation 4 was used in place of preparations 1 and 2, and in terms of improvement in moisturized feel and manageability in the same manner as in EXAMPLE 2 except that preparation 4 was used in place of preparation 2. As a result, the preparation 4-treated hair scored 4.9 points in slipperiness and finger combability, 4.8 points in moisturized feel and 4.9 points in manageability.

The hair warming tool according to the first aspect of the present invention makes various hair treatment preparations which enhance their effects under heat exerts their effects effectively and selectively on part of hair that particularly needs the treatment. With this tool, therefore, overcare on unnecessary part of hair is avoided. In treating damaged hair, in particular, since damage becomes more serious toward the tips, intensive treatment can be given only to the damaged part while leaving the non-damaged part untreated and thereby preventing overcare of the non-damaged part, making the non-damaged part look natural. Having a margin of prescribed width where no heating part is disposed, the hair warming tool is convenient and safe to use. That is, the tool is easy to fix with a fastening means at the margin and is prevented from causing discomfort or a burn due to direct contact of the heating part with the scalp.

The hair treating method according to the second aspect of the present invention makes various hair treatment preparations which enhance their effects under heat exert their effects securely and selectively on part of hair that particularly needs the treatment. It is only part of hair except near the roots that is wrapped in a warming tool, so that discomfort or a burn that might be caused by heat directly applied to the scalp during the treatment can be avoided. Thus, treatments with various hair treatment preparations can be carried out conveniently and safely.

In the present invention, since warming hair is achieved by wrapping with a warming tool of sheet form, overdrying as often results from drying with a hair dryer does not occur. Continuing warming even for a long time, for example longer than 30 minutes, does not result in damage or denaturation of hair. In case where all of hair is covered for warming, the scalp perspires due to the heat, usually requiring rinsing after the treatment. According to the present invention, perspiration of the scalp can be suppressed so that rinsing could be omitted.

The invention having been thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application No. 2001-55990 filed Feb. 28, 2001, which is incorporated herein by reference.

What is claimed is:

1. A hair warming tool of sheet form comprising:
   at least one heating part in the center thereof, the heating part including a heat generating material which contains iron powder and generates heat upon contact with air; and
   a margin disposed around said heating part, said margin being free of the heat generating material and configured to wrap hair adjacent to said heating part and to be held in place to maintain a wrapped state by a fastener connected to said margin,
   wherein the hair warming tool includes first and second sides, each of the first and second sides having a surface area of from 100 to 1200 cm$^2$, and the hair warming tool further includes an outermost base sheet adapted to contact said wrapped hair when in the wrapping state, said outermost base sheet comprising a water resistant material, said outermost base sheet being non-removably attached to said hair warming tool and the margin includes a seal at an outer perimeter of the margin, and the margin further includes a portion between the seal and the heating part, the portion including a first sheet separated from the outermost base sheet by an air gap,
   wherein a total area of the heating part, as viewed from the first side, extends across 10% to 40% of the surface area of the first side, and
   wherein a width of the margin as measured from an edge of the hair warming tool to the nearest heating part extends from 3 to 15 cm over a periphery of the hair warming tool.

2. A hair warming tool according to claim 1, which has a plurality of heating parts in which said tied hair is wrappable, and the plurality of heating parts are separated from each other by at least one open space.

3. The hair warmer according to claim 1, wherein the heating part includes a plurality of heating parts.

4. The hair warming tool according to claim 1, wherein the heat generating material is a composition comprising 40 to 60% iron powder, 1.0 to 3.0% sodium chloride, 1.0 to 5.0% activated carbon, 3.0 to 5.0% a water-absorbent polymer, and 3.0 to 10.0% vermiculite.

5. The hair warming tool according to claim 1, wherein the heat generating material is used in an amount of 0.05 to 0.3 g per cm$^2$ of the heating part.

6. The hair warming tool according to claim 1, wherein the water resistant material includes at least one of a synthetic resin, paper, metal and a non-woven fabric.

7. The hair warming tool according to claim 1, wherein the first sheet includes holes connecting the air gap in fluid communication with an area outside of the hair warming tool.

8. The hair warming tool according to claim 7, further comprising a second sheet disposed in direct contact with the first sheet and overlapping the first sheet.

9. The hair warming tool according to claim 8, wherein the margin is devoid of heat generating material.

10. The hair warming tool according to claim 9, wherein the first sheet is disposed on a first side of the at least one heating part, the outermost sheet is disposed on a second side of the at least one heat generating part, and the second side is opposite the first side such that the first sheet and outermost sheet sandwich the heat generating part.

11. A hair treating method which comprises:
    activating at least one heating part of a hair warming tool of sheet form including an outermost base sheet comprising a water resistant material, said heating part including a heat generating material, the hair warming tool including first and second sides, each of the first and second sides having a surface area of from 100 to 1200 cm$^2$, and the hair warming tool further including a seal, and a margin free of the heat generating material and disposed between the heating part and the seal, the margin including a first sheet separated from the outermost base sheet by an air gap;
    wrapping tied hair with said hair warming tool, the tool wrapped around the hair with the outermost base sheet facing and contacting the hair while leaving at least a part of the hair near roots unwrapped,
    wherein a total area of the heating part, as viewed from the first side, extends across 10% to 40% of the surface area of the first side, and
    wherein a width of the margin as measured from an edge of the hair warming tool to the nearest heating part extends from 3 to 15 cm over a periphery of the hair warming tool.

12. The hair treating method according to claim 11, which further comprises applying a hair treatment preparation containing at least one oiliness compound to the hair to be wrapped.

13. The hair treating method according to claim 12, wherein said hair treatment preparation further contains an organic acid.

14. The hair treating method according to claim 12, wherein said hair treatment preparation has an emulsified state that is broken at 55 to 60° C.

15. The method according to claim 14, wherein the emulsified state is broken at a demulsifying temperature that is the temperature of an endothermic peak of a differential scanning calorimetry curve.

16. The method according to claim 15, wherein the curve is measured at a temperature rise rate of 3 degrees C/min.

17. The hair treating method according to claim 11, which further comprises applying a hair treatment preparation having a pH of 2 to 4.5 to the hair to be wrapped.

18. The hair treating method according to claim 11, wherein the water resistant material includes at least one of a synthetic resin, paper, metal and a non-woven fabric.

19. A method for treating hair, comprising:
obtaining a portion of hair;
activating a heat generating portion of a hair warmer, the heat generating portion including a heat generating material;
wrapping the portion of hair in said hair warmer including an outermost base sheet comprising a water resistant material, the outermost base sheet facing and contacting the portion of hair as the portion of hair is wrapped with the hair warmer;
applying an oiliness compound to the portion of hair before the wrapping,
providing a seal sealing a first sheet to the outermost sheet around a perimeter of the outermost sheet, and
providing an air gap between the first sheet and the outermost sheet in a margin between the seal and the heat generating portion, said margin being free of the heat generating material and configured to wrap hair adjacent to said heating part and to be held in place to maintain a wrapped state by a fastener connected to said margin,
wherein the hair warmer includes first and second sides, each of the first and second sides having a surface area of from 100 to 1200 cm$^2$,
wherein a total area of the heat generating portion, as viewed from the first side, extends across 10% to 40% of the surface area of the first side, and
wherein a width of the margin as measured from an edge of the hair warming tool to the nearest heating part is from 3 to 15 cm over a periphery of the hair warming tool.

20. The method according to claim 19, wherein the oiliness compound has an emulsified state that is broken between 55° C. and 60° C.

21. The method according to claim 20, wherein the emulsified state is broken at a demulsifying temperature that is the temperature of an endothermic peak of a differential scanning calorimetry curve.

22. The method according to claim 21, wherein the curve is measured at a temperature rise rate of 3 degrees C/min.

23. The method according to claim 19, wherein the oiliness compound includes an organic acid.

24. A method for treating hair, comprising:
obtaining a portion of hair;
activating a heat generating portion of a hair warmer, the heat generating portion including a heat generating material;
wrapping the portion of hair in said hair warmer including an outermost base sheet comprising a water resistant material, the outermost base sheet facing and contacting the portion of hair as the portion of hair is wrapped with the hair warmer;
applying a composition having a pH between 2 and 4.5 to the portion of hair before the wrapping,
providing a seal sealing the first sheet to the outermost sheet around a perimeter of the outermost sheet, and
providing an air gap between the first sheet and the outermost sheet in a margin between the seal and the heat generating portion, said margin being free of the heat generating material and configured to wrap hair adjacent to said heating part and to be held in place to maintain a wrapped state by a fastener connected to said margin,
wherein the hair warmer includes first and second sides, each of the first and second sides having a surface area of from 100 to 1200 cm$^2$,
wherein a total area of the heat generating portion, as viewed from the first side, extends across 10% to 40% of the surface area of the first side, and
wherein a width of the margin as measured from an edge of the hair warming tool to the nearest heating part is from 3 to 15 cm over a periphery of the hair warming tool.

25. The method according to claim 24, wherein the composition has an emulsified state that is demulsified between 55° C. and 60° C.

26. The method according to claim 25, wherein the demulsifying temperature is the temperature of an endothermic peak of a differential scanning calorimetry curve.

27. The method according to claim 26, wherein the curve is measured at a temperature rise rate of 3 degrees C/min.

* * * * *